United States Patent [19]

Niwa et al.

[11] 4,429,691

[45] Feb. 7, 1984

[54] METHOD FOR FILLING IN DEFECTS OR HOLLOW PORTIONS OF BONES

[75] Inventors: Shigeo Niwa, Aichi; Kazuhiko Sawai; Shinobu Takahashi, both of Nagoya; Hideo Tagai, Tokyo; Mikiya Ono, Saitama; Yoshiaki Fukuda, Saitama; Hiroyasu Takeuchi, Saitama, all of Japan

[73] Assignee: Mitsubishi Mining and Cement Company, Ltd., Tokyo, Japan

[21] Appl. No.: 342,259

[22] Filed: Jan. 25, 1982

Related U.S. Application Data

[62] Division of Ser. No. 191,894, Sep. 29, 1980, abandoned.

[30] Foreign Application Priority Data

Oct. 8, 1979 [JP]  Japan ................................. 54-128821

[51] Int. Cl.³ .......................... A61F 1/00; C01B 25/32
[52] U.S. Cl. ................................ 128/92 C; 128/92 G; 423/308; 423/309; 423/311
[58] Field of Search ....................... 423/308, 309, 311; 3/1.9; 128/92 G, 92 C

[56] References Cited

U.S. PATENT DOCUMENTS

| | | | |
|---|---|---|---|
| 3,737,516 | 6/1973 | Jenner | 423/308 |
| 4,046,858 | 9/1977 | Barsa et al. | 423/311 |
| 4,149,894 | 4/1979 | Ebihara et al. | 423/308 |
| 4,309,488 | 1/1982 | Heide et al. | 128/92 C |

FOREIGN PATENT DOCUMENTS 1455360  11/1976  United Kingdom ................ 423/311

Primary Examiner—O. R. Vertiz
Assistant Examiner—Wayne A. Langel
Attorney, Agent, or Firm—Jordan and Hamburg

[57] ABSTRACT

A filler for filling in defects or hollow portions of bones to coalesce with the bone tissues is provided which comprises powders of a calcium phosphate compound having the apatite crystalline structure of each crystal grain size of from 50 Ư to 10 microns and represented by the following general formula of $Ca_m(PO_4)_nOH$ ($1.33 \leq m/n \leq 1.95$); and said powders being adapted for filling in a fluidized or plasticized state. A method of treating a bone with the filler is also provided wherein at least a portion of said filler is filled in to reach the bone-marrow cavity of said bone.

16 Claims, 5 Drawing Figures

METHOD FOR FILLING IN DEFECTS OR HOLLOW PORTIONS OF BONES

This is a division, of application Ser. No. 191,894, filed Sept. 29, 1980 now abandoned.

BACKGROUND OF THE INVENTION

1. Field of the Invention

The present invention relates generally to a medical material, and particularly to an inorganic filler to be filled in defects or hollow portions formed by a removal operation of bone tumor or other causes in the bones of a living body to promote formation of new bone tissue at the filled portions and to coalesce with the bone tissue after the injured portions are completely cured. The present invention also relates to a medical treatment for curing the injured bones by the use of said filler.

2. Prior Art

In the surgical or orthopedic field, defects or hollow portions of bones are frequently formed by highly complicated fractures or a removal operation of bone tumor, and such defects or hollow portions should be cured by symphysis. In the prior art method, a cancellous bone is taken up from flank bones or other bones of the patient per se to be filled in the injured portion of bone to promote the cure of bone tissue. However, this prior art method is disadvantageous in that the patient suffers a greater pain from cumbersome labours necessitated in the operation, since a bone tissue other than the injured portion is taken out for use. Moreover, a sufficient amount of autoplastic bone cannot always be taken up from the patient's body for filling in a large defect or hollow portion of bone, and a certain substitute material is required to supplement the shortage of the required bone tissue in such a case.

Other than the method of autoplastic filling, there are a homogeneous bone implantation method and a heterogeneous bone implantation method. As to the homogeneous bone implantation method, uses of frozen bones and decalcified bones have been investigated but have not yet reached the stage of clinical practice. In the heterogeneous bone implantation method, a so-called keel bone, which is prepared by removing proteins from a bone of cattle, is used in some cases. However, both of these known methods are not only accompanied with foreign body reactions but also lack osteogenic capacity, so that the post-operation course is not always good. Accordingly, there is an increasing demand for an artificial filler material for filling in defects or hollow portions of bones which is excellent in compatibility with the living body and has high osteogenic capacity to promote the bone-forming reaction at the filled portion and at the vicinity thereof to accelerate curing of the structure and function of injured bone tissue.

With the aim to reducing the period of time required for curing the fractured bone, an internally fixing method is sometimes adopted wherein the fractured bone is directly fixed by the use of a metal plate, nail or screw. However, adopting such a method, there is often a case where so lengthy a time as six months or a whole year is necessary for complete curing. Furthermore, if the internally fixing method is adopted, the materials used for internal fixing shall be removed from the patient's body after the fractured bone is cured, and thus the patient suffers tremendous physical, psycological and economical burdens. If a filler material of the aforementioned kind for promoting the osteogenic capacity and for accelerating the remedy or cure of the fractured or injured portion is developed, it will be made possible to attain the object of therapy for a short period of time without the application of the internally fixing method. The filler material of the aforementioned kind may be also used for the therapy of pseudoarthrosis. It is, therefore, considered that the development of such filler is of great medical value and contributes to welfare of humankind.

On the other hand, various metals and plastics materials have hitherto been used as the substitute materials for hard tissues of living body. However, these conventional materials are apt to be dissolved or deteriorated under the severe environment in the living body and are often accompanied with poisonous actions or foreign body reactions. For this reason, biomaterials of ceramics which have improved compatibilities with a living body attracted public attention in recent years. At the present time, an artificial bone, an artificial joint and an artificial radix dentis made of single crystalline or polycrystalline alumina ($Al_2O_3$) and an artificial radix dentis made of sintered calcium tertiary phosphate ($Ca_3(PO_4)_2$) or sintered hydroxyapatite ($Ca_5(PO_4)_3OH$) have been proposed. It has been reported that these materials are excellent in compatibility with a living body, for example, no appreciable formation of membrane caused by the foreign body reaction is observed when a sintered article of hydroxyapatite is implanted in a bone of a living body, which shows the direct connection between the sintered article and the bone tissue. However, these implantation materials are disadvantageously too hard and fragile, similarly as is the case of common ceramic materials, and should be improved in toughness and impact strength in order to use in the form of artificial bone or artificial radix dentis practically.

OBJECTS AND SUMMARY OF THE INVENTION

An object of the present invention is to provide a filler for filling in defects or hollow portions of bones which is excellent in compatibility with the living body and free from foreign body reaction.

Another object of the present invention is to provide a filler for filling in defects or hollow portions of bones which can facilitate formation of new bone tissue remarkably and can considerably cut down the period of time required for curing the structure and function of bone tissue.

A further object of the present invention is to provide a filler for filling in defects or hollow portions of bones which can coalesce with the bone tissue to form an integral autoplastic bone.

Another object of the present invention is to provide a method of treating bones with a filler for facilitating formation of new bone remarkably and for leaving an adequate quantity of bone at the requisite portion.

A further object of the present invention is to provide a method of treating bones with a filler for curing the structure and function of bone tissue not accompanied with any foreign body reaction for a short period of time.

Yet a further object of the present invention is to provide a simple method for curing the defects or hollow portions of bones.

According to the present invention, there is provided a filler for filling in defects or hollow portions of bones to coalesce with the bone tissues, comprising powders of a calcium phosphate compound having the apatite crystalline structure of each crystal grain size of from 50 Å to 10 microns and represented by the following general formula of $Ca_m(PO_4)_nOH$ ($1.33 \leq m/n \leq 1.95$), and said powders being adapted for filling in a fluidized or plasticized state.

Accordingg to another aspect of the present invention, there is provided a method of treating bones with the aforementioned filler, wherein at least a portion of said filler is filled in to reach the bone-marrow cavities of said bones.

DESCRIPTION OF THE INVENTION

Figure 1:
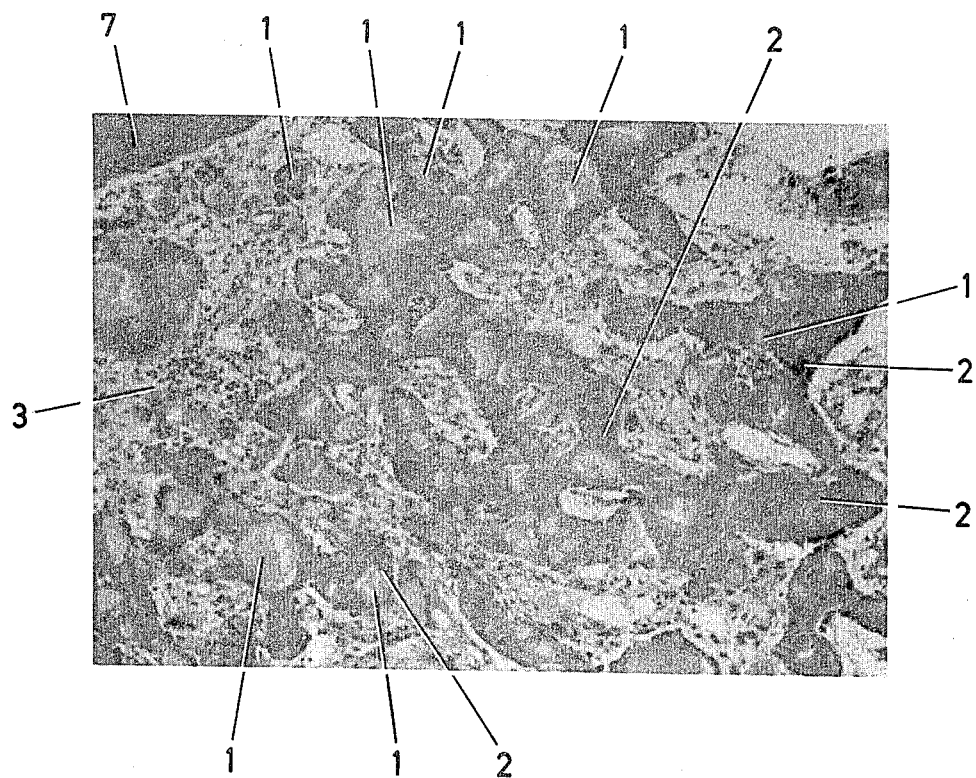
FIG. 1 is a microphotograph of a crosswise section of a decalcified specimen showing the femur of a rabbit provided with a hole filled with the filler of the invention, the femur being taken out of the rabbit killed after the lapse of one week from the time of the implantation.

Various forms of calcium phosphate compounds are known including a compound referred to as hydroxyapatite and represented by the rational formula of $Ca_5(PO_4)_3OH$. A group of minerals referred to as generally apatite is represented by the rational formula of $M_m(RO_4)_nX$, wherein the site shown by M is occupied by a divalent cation such as $Ca^{2+}$, $Sr^{2+}$, $Ba^{2+}$, $Pb^{2+}$, $Zn^{2+}$, $Mg^{2+}$ and $Fe^{2+}$ or a trivalent or monvalent cation such as $Al^{3+}$, $Y^{3+}$, $La^{3+}$, $Na^+$, $K^+$ and $H^+$, the site shown by $RO_4$ is occupied by an anion such as $PO_4^{3-}$, $VO_4^{3-}$, $BO_3^{3-}$, $CrO_4^{3-}$, $SO_4^{2-}$, $CO_3^{2-}$ and $SiO_4^{4-}$ and the site shown by X is occupied by an anion such as $OH^-$, $F^-$, $Cl^-$, $O^{2-}$ and $CO_3^{2-}$. Many compounds having resembling crystalline structures are included in this group. The aforementioned hydroxyapatite is a typical compound having the apatite crystalline structure and the composition theoretically represented by $Ca_5(PO_4)_3OH$. However, the composition of this compound produced by an artificial synthesis is not always represented by the theoretical formula but is represented by the formula of $Ca_m(PO_4)_nOH$ wherein the molar ratio of m/n ranges within $1.33 \leq m/n \leq 1.95$. Although many hypotheses have been presented with regard to the phenomenon of variation of the value m/n (molar ratio) in a wide range, this is considered due to the particular crystalline structure of the apatite compound. If the composition is within the range as set forth above, the aimed compound may be artificially synthesized while avoiding the intermingled presence of different phases. In the present invention, the compounds having the compositions within the range as set forth above and having the apatite structure from the crystallographical viewpoint are referred to as the calcium phosphate compounds having the apatite crystalline structures or the apatite calcium phosphate compounds which include hydroxyapatite of the theoretical composition. The calcium phosphate compounds represented by the formula of $Ca_m(PO_4)_nOH$ are readily modified by incorporating various different ions at the sites of Ca, $PO_4$ and OH. It is to be noted here that the compounds used in the present invention include such modifications modified by the presence of any different ions so far as the compatibility with the living body is not lost and the composition range of m/n is maintained within $1.33 \leq m/n \leq 1.95$.

The crystal grain size (or crystallite) of the apatite calcium phosphate compound used in the present invention should be within the range of from 50 Å to 10 microns. A particularly preferred range is more than 200 Å and less than 3 microns. The crystal grain size of the hydroxyapatite forming the hard tissue of the living body ranges from several hundreds to several thousands Å. It is desirous that the crystal grain size of the powders used in the filler of the present invention approximates the crystal grain size of the hydroxyapatite constituting the living body in order to promote formation of new bones at the vicinity of particles of the filler filled in the defects or hollow portions and to form a uniform living tissue as the result of the coalescence between the new bones and the particles of the filler. If the crystal grain size of the apatite calcium phosphate compound is more than 10 microns, the formation of new bones is retarded resulting in delayed curing of the defects and further the newly formed bones lack uniformity. On the contrary, if the crystal grain size is less than 50 Å, the filler particles in the new bone is less crystallizable so that the coalescing capacity thereof does not reach the satisfactory level.

It is preferred that the particle size distribution of the apatite calcium phosphate compound used in the present invention is such that powders each having the particle size of 300 microns or less occupy 90% or more of the total weight. If the content of particles having the particle size of 300 microns or less does not reach 90% by weight, when the filler is added with water or an isotonic sodium chloride solution to be fluidized or plasticized, the particles tend to separate from water. As a result, there is a fear that the filler cannot be plasticized or the particles are sedimented only to the lower portion of the hollow portion to result in formation of unfilled vacancy at the top portion when the filler is filled in the living body. As far as the particle size distribution is within the range as aforementioned, the presence of some quantities of larger particles having the particle size of about several mm may be allowed.

Natural materials, for example, bone ashes prepared by baking bones of animals may be used as the apatite calcium phosphate compound of the present invention, and synthetic materials prepared by the known wet process, dry process and hydrothermal process may also be used for the same purpose. The apatite calcium phosphate having a composition within the range as defined above and synthesized by the wet process is generally obtained in the form of precipitate composed of minute particles while being somewhat altered depending on the temperature and other conditions at the synthesis step, and may be separated from the solvent by means of filtration or centrifugal separation and then dried at a temperature of lower than 500° C. followed by pulverization to form a material of impalpable powder. This powder form material may be directly fluidized or plasticized, as will be described hereinafter, to be filled in defects or hollow portions of bones as a filler having the osteogenic capacity. However, the aforementioned material prepared by the wet process is preferably calcined at a temperature ranging with 500° C. to 1100° C., preferably 700° to 900° C., optionally subjected to a pulverization treatment to form a powdered material, and then fluidized or plasticized for use as a filler for filling in defects or hollow portions of bones, in order to improve the crystallinity of the particles and to sufficiently sterilize by heating for preventing infection by bacteria and for preventing foreign body reaction caused by organic materials. Calcination effected at a temperature of not higher than 500° C. is unsatisfactory, since no appreciable growth of particles takes place. As the calcination temperature is raised to higher than 900° C., growth of crystal grain becomes somewhat excessive. If the heating temperature exceeds 1100° C., the particles are rapidly sintered with each other to form lumps.

An apatite calcium phosphate compound having a relatively coarse crystal grain size is prepared by the dry process or by the hydrothermal synthesis process. The case where lumps are included, such lumps are crushed to obtain powders or particles. If these powders or particles are heated again at a temperature of lower than 1100° C. to be sterilized, they can be smoothly filled in defects or hollow portions of bones to fulfill their functions as the filler.

The powders or particles prepared by any of the aforementioned wet, dry and hydrothermal synthesis processes may be molded using a hydraulic press and then sintered, optionally followed by pulverization, to produce porous particles. A preferable sintering temperature range is 1100° C. to 1350° C., and particularly preferred sintering temperature range is 1200° to 1300° C. When the temperature is raised to higher than 1100° C., particles are fused with each other to form larger particles having pores or voids. This tendency is accelerated as the temperature is raised to higher than 1200° C. As the temperature is raised to higher than 1300° C., the apatite calcium phosphate compound begins to be converted to calcium tertiary phosphate and the decomposition is accelerated seriously if the temperature reaches to 1350° C. If such porous particles are used as the filler, the living tissue is allowed to penetrate into the pores of the particle. As a result, the growth of new bone is promoted by the use of larger particles provided with pores.

The powders prepared by any of the aforementioned synthesis processes and/or the particles obtained by calcinating or sintering the powders are fluidized or plasticized by the addition of a liquid, such as water or an isotonic sodium chloride solution, and then filled in the defects or hollow portions of bones. By fluidizing or plasticizing the powders or particles, the fine powders are prevented from scattering to adhere to undesired portions of the patient's body other than the injured portions so that any adverse influence caused by adherence of scattering powders is excluded. Another advantage attained by the use of a fluidized or plasticized filler is that the defects or hollow portions of bones are wholly and uniformly filled with the filler by a simple injection operation. The quantity of the liquid to be added is varied depending on the particle size of the used filler and the presence or absence of pores. If water or an isotonic sodium chloride solution is used, the added quantity thereof may be determined within the range in which separation of water does not occur and the powders or particles are sufficiently plasticized to be easily filled in the hollow portions. In general cases, 0.1 to 2 parts by weight of water or an isotonic sodium chloride solution is added to 1 part by weight of the filler.

The aforementioned powders or particles may be put into a granulator, for example a rolling granulating machine, and added with a liquid, such as water or isotonic sodium chloride solution, to form granules. A preferred shape of granules is spherical or pilular to facilitate filling, and the diameter of granules may be varied depending on the dimensions of defects or hollow portions in which the granular filler is filled with the generally preferred diameter ranges from 0.5 to 5 mm. The quantity of the liquid used for granulation preferably ranges from 20 to 50% by weight based on the total weight. These granules may be stored in a container, such as a glass bottle, with a seal and poured into the injured portion when in use. By the use of granular filler, the hollow portion can be uniformly filled with such granules with voids left therebetween. If dense filling is desired, the granules may be simply pushed into the hollow portion using a bar or like implement since the granules are plastic. This plastic granules have advantages that they can be easily handled when in use and that the filling density may be controlled as desired.

The aforementioned granules may be sintered at 1100° to 1350° C., preferably 1200° to 1300° C. to form sintered beads. The sintering temperature is limited as aforementioned for the same reason described hereinbefore in the case of sintering the powders. Since the thusly formed sintered beads are porous, the living tissue is allowed to penetrate into the pores, so that formation of new bone at the vicinity of particles forming the sintered bead is remarkably promoted and the sintered material coalesces with the new bone rapidly. In order to make use of this advantage, the porosity of the sintered beads is preferably more than 30%. If the porosity is not more than 30%, the advantageous effect is diminished. The living tissue can easily penetrate into the pores having the diameter of larger than 100 microns. Accordingly, it is preferred that more than 50% of the pores have the diameter of larger than 100 microns. This sintered beads are preferably spherical, so that they are fluent nevertheless individual beads are solid. Therefore, it may be said that this sintered beads can be fluidized, as referred to in the present invention, to be poured into the injured portion to fill the same easily and immediately. Moreover, the particle size of these beads can be freely adjusted at the bead formation step. If the particle size distribution is controlled in a narrow range, the injured portion of bone can be filled at low density with increased voids. On the contrary, if the particles size distribution is spread and beads having different diameters are included, relatively high density filling may be realized. Generally speaking, completion of new bone is accelerated when a relatively large space is void.

The aforementioned porous sintered beads may be used in the dry state as they are, since they are fluent as mentioned hereinabove. However, the porous sintered beads may be added to the powder form filler and then added and kneaded with water or an isotonic sodium chloride solution for use in the form of a paste. If the porous beads are mixed in the paste, the porosity of the entire paste may be increased. The sintered beads may be added in a ratio at which the fluidity or plasticity of the filler of paste form is not lost, and the preferred ratio being less than 30% by weight based on the total weight of the paste.

As the filler for filling in defects of bones according to the invention, the aforementioned apatite calcium phosphate compound may be used singly. However, it is preferred that a cancellous bone obtained by crushing a bone may be mixed together to further increase the bone formation speed. The cancellous bone of autoplastic origin has been conventionally used singly as a filler for filling in a defect of bone. However, there is often a case where a sufficient quantity of cancellous bone enough for filling the defect cannot be taken up, or it is desired that the quantity of cancellous bone of autoplastic origin is reduced as small as possible. The apatite calcium phosphate compound of the present invention may be mixed at a desired ratio with the autoplastically obtained cancellous bone. On the other hand, a bone of foreign origin has hitherto been limitedly used singly so as to avoid the foreign body reaction or other problems. However, when the bone of foreign origin is mixed with the apatite calcium phosphate compound of the present invention, the adverse reactions including the foreign body reaction can be considerably reduced to facilitate therapy. The mixing ratio of bone of foreign origin is preferably less than 50% by weight of the total weight, and a particularly preferable mixing ratio is less than 20% by weight. If more than 50% by weight of bone of foreign origin is mixed, reduction in adverse reaction becomes unsatisfactory nevertheless the bone formation speed is increased. Similarly as in the case where the apatite calcium phosphate compound is used singly, the mixture of the compound and the cancellous bone may be added with water or an isotonic sodium chloride solution to be fluidized or plasticized to prepare a filler to be filled in a defect of bone.

The filler of the invention having the construction as aforementioned, has the fluidity or plasticity so that it can be uniformly and wholly filled in any defects or hollow portions of bones irrespective of how complexly shaped they are. Furthermore, the filler of the invention is different from the conventional implant materials made of integral articles in that it is made of powders, which are added in a fluidized or plasticized state prior to filling in an injured portion of bone, so that the powders are diffused in the implanted living body uniformly and the surfaces of the powders are readily covered with the growing tissue. More detailed description of the characteristic feature of the filler of the present invention in this respect will be given as follows. When the apatite calcium phosphate compound is filled in the injured portion of bone directly in the form of powder, the particles tend to coagulate with each other to form aggregations to hinder the growing tissue from penetrating inbetween the particles. However, the filler of the present invention is added in a fluidized or plasticized state to allow the particles to be dispersed in a relatively dense condition, as shown in FIG. 1, whereby the growing tissue is allowed to penetrate inbetween the particles. It is an important feature of the present invention that the particles are not coagulated but dispersed in a dense condition. Fine powders have the water-repellent property in the dry state to hinder the living tissue from diffusing in the dry filler. However, since the filler of the invention is used after being wetted with water or an isotonic sodium chloride solution or after being granulated the living tissues diffuse easily in the filler filled in the defect of bone. As a result of the combined function of dispersion of powders and diffusion of living tissues, formation of new bone is promoted. More specifically, when the filler of the invention is filled in a defect or hollow portion of bone, new granulation tissues surround the particles after the lapse of a short period of time and the particles are present while being dispersed in the granulation tissues. It should be noted here that no giant cells caused by foreign bodies appear at all, since the powders of the present invention made of the apatite calcium phosphate compound have remarkably improved compatibilities with the living tissues. Under such condition, osteoid with attendant osteoblast adheres to the peripheral portions of the particles without forming membranes caused by foreign bodies, and new bone tissues are rapidly formed from the peripheral surfaces of the particles towards their vicinities and the granulation tissues are changed to the connection tissues with the lapse of time. The filler of the invention composed of powders has a large surface area to increase the new bone formation speed considerably. The new bone tissues formed on the surfaces of the particles continue to grow and cross-link the particles which are present by close spacings. As the cross-linking structures grow, new cancellous bones are formed here and there and finally all of the filler particles are connected with each other by the newly formed dense cancellous bone integrally. As a result, an integral structure is formed, where powder particles of the apatite calcium phosphate compound are dispersed in a newly formed bone beam which has a low calcium density. Then, the new bone becomes denser to form a new bone tissue having the same composition as that of the surrounding old bone for covering the defect or hollow portion of bone. Finally, the injured portion is completely cured without any appreciable difference, as the particles of the filler assimilate with the new bone. However, formation of bone tissue stimulated by the filler of the invention does not proceed too far beyond the functional requirement generally required for normal bone tissue. In this connection, the filler of the invention has another advantage in that the portions thereof filled in the unnecessary portions are absorbed in the living body. As has been mentioned hereinabove, new bone tissues are initially formed on the surfaces of the particles of the filler. Accordingly, it is preferred that the specific surface area of the particles is increased and a larger number of particles is present in a unit volume, in order to increase the bone formation speed. Also, the spacings between the particles should be preferably closer at some extent for allowing the new bone to cross-link the particles to form a bone beam and further to connect the entire structure to form a cancellous bone. The speed of assimilation is accelerated as the particle size is smaller, since the compound is assimilated with the newly formed bone from the surfaces of the particles toward the inner portions thereof. In view of the foregoing, smaller particles are preferred to increase the bone formation speed. However, since osteogenic materials shall be fed from the living body inbetween the particles, the particle size is spontaneously limited and the lower limit of the particle size is determined by the supply of the osteogenic materials.

As will be clearly understood from the foregoing description with regard to the construction, action and function of the present invention, the present invention is entirely different from the conventional technical concept of providing substitute materials for hard tissues including artificial bones and artificial radix dentis which are made of sintered single crystalline alumina (sapphire), sintered polycrystalline alumina or sintered hydroxyapatite and developed with the aim to simply avoiding the foreign body reaction between the bone tissue and to improving the adherence property. In other words, the filler of the present invention promotes the regeneration or self-curing action of the patient's bone tissue of itself taking place at the defects or hollow portions of bones, and the filler composition per se is incorporated into the bone tissue and coalesces therewith. For this reason, the inherent strength of the material used in the present invention is out of the question.

Although an appreciable effect can be obtained only by filling the filler of the invention in the defects or hollow portions of bones formation of new bone will be further promoted if a portion of the filler reaches the bone marrow cavity. New bones are initially formed at the portions of defects where the filler particles contact with the bone marrow and then gradually grow into the hollow portions. However, the newly formed bone tissue formed in the bone marrow cavity and essentially to be discarded ultimately is absorbed in the living body by the action of osteoblasts and the requisite amount of new bone is left only at the necessary portion. According to this method, it is possible to ensure curing and to shorten the time required for therapy. The filler according to the invention exhibits its function only when it is used under the environment of a living body where the bone tissue is to be formed, in other words only when it is used at the defects or hollow portions of bones. The result of the experiment, where the filler of the invention is injected into the femoral muscle tissue of a rabbit, reveals no sign of bone formation in the muscle tissue after all.

As has been described in detail hereinbefore, the powder or particle form apatite calcium phosphate compound according to the invention has a remarkably improved compatibility or adaptability with the living tissues and also has an excellent osteogenic capacity. Moreover, the filler of the invention is advantageous in that it coalesces with the bone tissue to be incorporated thereinto and exhibits a synergistic action to promote the regeneration or self-curing function of the bone tissue per se remarkably. The filler of the invention is used in a simple manner and the materials for the filler can be supplied from inexhaustible sources to make it possible to supplement the shortage in supply of autoplastic bone.

The filler of the invention can be used not only for filling in defects or hollow portions of bones to remedy the bone tumor or the fractured bone and in the arthroplasty operation, the spinal fusion operation and the intervertebral disk fusion operation, but also for filling in the injured portion formed in the processes alveolaris caused by pyorrhea alveolaris.

EXAMPLES OF THE INVENTION

The present invention will now be described more specifically by referring to several examples thereof. However, it should be appreciated that the present invention is not limited only to the examples given below.

Throughout the specification and appended claims, the crystal grain size of the calcium phosphate compound having the apatite crystalline structure will be indicated by the value of each crystallite in the direction of C-axis obtained from the half-width of the peak of diffraction measured by the X-ray diffractiometry wherein the spacing (002) is $2\theta = 25.9°$ when the crystal grain size is less than 0.1 microns; and will be indicated by the practically determined average diameter of crystal grains along the longitudinal direction measured by using a scanning electron microscope, when the crystal grain size is more than 0.1 microns.

EXAMPLE 1

An apatite calcium phosphate compound (Molar Ratio of Ca/P = 1.65) was synthesized by a wet process wherein phosphoric acid was dropwise added into a solution of calcium hydroxide. The dried powders of this compound were calcined at 850° C. for 5 hours. The size or dimensions of crystallites was measured by the X-ray diffractiometry to reveal that the average diameter of crystallite along the c-axis was about 600 Å and the average diameter of crystallite along the a-axis was about 500 Å. Coarser powders were removed such that all particles pass through a net of 300-micron meshes. The thus obtained powders were added with an isotonic sodium chloride solution to form a paste which was injected into the bone-marrow of the femur of a rabbit. The injected portion was kept observed. Formation of new bones in the neighbourhood the injected powders was observed after only one week from the time of injecting the paste of the apatite calcium phosphate compound, and no appreciable sign of foreign body reaction was observed at all. Then, the formed new bones were rapidly grown and it was observed that the particles composed of said compound were entirely incorporated into the newly growing bones and coalesced with the bone tissue. As will be apparent from the foregoing, the powders composed of said compound exhibits a remarkable osteogenic capacity which may be deemed as the particular effect of the apatite calcium phosphate compound when compared to the result of a similar comparative experiment wherein powders of alumina were used.

EXAMPLE 2

Each of the powders of the compounds synthesized by the wet processes and each having the ratio of m/n of 1.38, 1.56, 1.73 and 1.89 was calcined at 850° C. for 2 hours. The crystal grain sizes of these samples determined by measuring the diameters of crystallites by means of the X-ray diffractiometry were as follows:

| m/n | Average Diameter along the c-Axis | Average Diameter along the a-Axis |
| --- | --- | --- |
| 1.38 | 580 Å | 400 Å |
| 1.56 | 640 Å | 450 Å |
| 1.73 | 720 Å | 520 Å |
| 1.89 | 800 Å | 600 Å |

Every calcined powders were screened to obtain sample powders of less than 149 microns in size. Every powders were subjected to the X-ray diffractiometry to ascertain that all of these powders showed the diffraction pattern of hydroxyapatite and did not contain any other compounds. In accordance with the general procedure as set forth in Example 1, each of the powders was injected into the bone-marrow of the femur of a rabbit, and the formation of new bone at the injected portion was observed to ascertain that the function of each of these powders on the formation of bone tissue was equivalent to that observed in Example 1.

As has been described hereinbefore, the compositions of the apatite calcium phosphate compounds artificially synthesized are not always represented by the theoretical rational formula of $Ca_5(PO_4)_3OH$, but may be represented by the general formula of $Ca_m(PO_4)_nOH$ wherein the ratio of m/n, i.e. the molar ratio of Ca to P, varies within the range of from 1.33 to 1.95. In the present invention, all such compounds having the compositions as mentioned above are inclusively referred to as apatite calcium phosphate compound. When reviewing the results of this Example, it will be reasonably seen that every such compounds having the compositions as defined above exhibit similar effects to those obtained in the animal experiment shown in Example 1.

EXAMPLE 3

The powders used in Example 1 and composed of the apatite calcium phosphate compound having the molar ratio of m/n=1.65 and synthesized by the wet process were sufficiently dried at 110° C., and then screened to obtain a sample which passed a net of 149-micron meshes. The dried and screened powders were molded by compression molding to form a rectangular parallelpiped of 2×3×5 cm in dimension and having a porosity of about 50%. This rectangular parallelpiped was sintered in air at 1300° C. for 2 hours to from a sintered body having a density of about 95% of the theoretical density. The sintered body was crushed and pulverized, and then the pulverized particles were fractionized to obtain another sample having a particle size distribution of 0.3 to 0.04 mm. These two samples, i.e. the dried powder sample and the sintered sample, were subjected to similar animal experiments as conducted in the preceding Examples where the calcined powders were used. The results of the animal experiments showed that new bones were formed rapidly in the neighbourhood of dried powders and also in the neighborhood of sintered granules, similarly as in the preceding Examples.

Comparison was made between the bone tissue formation speed obtained by the use of the calcined powders as in Examples 1 and 2, the bone tissue formation speed obtained by the use of the dried powders as in Example 3 and the bone tissue formation speed obtained by the use of the sintered granules as in Example 3 to learn the effects of calcination and sintering in cases where the apatite calcium phosphate compound synthesized by the wet process is used. The result of comparison showed that the calcined powders were the most excellent, the sintered granules occupied the next best place and the dried powders were somewhat inferior to the other two. According to the X-ray diffractiometry analysis, each of the dried powders was composed of fine crystallites each having a dimension (along the C-axis) of 50 to 300 Å and each of the calcined powders was composed of crystallites each having a dimension (along the C-axis) of about 200 to 1000 Å whereas the crystal grain size of each of the sintered granules used in this Example ranges from 0.5 microns at the minimum to 7.5 microns at the maximum, the average size being 5 microns, as determined by a scanning electron microscope.

It should be clearly understood from these results that the powders or granules of a calcium phosphate compound substantially composed of hydroxyapatite crystals and represented by the formula of $Ca_m(PO_4)_nOH$ having the molar ratio of $1.33 \leq m/n \leq 1.95$ have excellent osteogenic capacity of themselves to remarkably promote the regeneration of the bone tissue when they are filled in any defect or hollow portion of bone. It will be also understood that the aforementioned compound is made of the same inorganic material forming the bone tissue of the living body so that the compound coalesces with the surrounding bone tissue as the new bone grows to be calcificated. Any apatite calcium phosphate compounds may be used as the starting material for the filler of the present invention irrespective of the synthesis processes employed for preparing the same. In addition to the powders synthesized by said wet process, powders or particles prepared by the dry process of the hydrothermal process can be used to fill in the defects of bones. When any of the apatite calcium phosphate compounds synthesized by various processes and subjected to after-treatments is used, the new bone formation speed at the vicinity of particles varies depending on the grain size of crystals constituting individual powders of said compound. For this reason, it is not preferred that the grain size of the crystals in the powder becomes too coarse, and the crystal grain size shall be limited within the range of from 50 Å to 10 microns according to the technical concept of the invention. It is preferred to use the powdered product obtained by calcining the compound synthesized by the wet process at a temperature of 500° to 1100° C., when it is required to promote the formation of new bone rapidly. The filler prepared by sintering the apatite calcium phosphate compound at a temperature in the range of from 1100° to 1350° C. and the filler prepared by the dry synthesis process might contain a small amount of crystal of calcium tertiary phosphate ($Ca_3(PO_4)_2$) which has not the apatite crystalline structure. About 3 to 5% by weight of calcium tertiary phosphate was mixed in the sintered powders used in this Example and detected by the X-ray diffractiometry analysis. However, the intermingled calcium tertiary phosphate does not seriously affect the essential function of the filler of the invention as far as the mixing ratio thereof is limited to about 5% by weight and the filler containing a small amount of calcium tertiary phosphate may be used as the filler of the invention without any adverse influence.

EXAMPLE 4

740 g of calcium hydroxide (a special grade chemical reagent produced by Junsei Kagaku K.K.) was suspended in 20 liters or water. An about 30 wt% phosphoric acid solution (prepared by diluting a special grade chemical reagent produced by Wako Junyaku K.K.) was dropwise added to the suspension while agitating the suspension and maintained at 40° C. until the pH value of the liquid reached 8.8. Agitation was continued for additional one hour, and then the suspension was allowed to stand stationarily at 40° C. for 48 hours to age the same. A precipitate of apatite calcium phosphate was obtained. This precipitate was filtered by the use of a suction filter, rinsed and then dried in a hot air circulation drier maintained at 105° C. for 24 hours to form a cake which was pulverized in a ceramic pot mill to obtain dried powders having the particle size passing through a net of 300-micron meshes. Then, the powders were calcined in an electric furnace maintained at 800° C. for 6 hours. The crystal grain size of the calcined powders was measured by the X-ray diffractiometry to find the diameter of crystal grain along the C-axis was about 550 Å and that the long the a-axis was about 470 Å. After cooling outside of the furnace, the calcined powders were screened using a net of 149-micron meshes to remove coarser particles and sterilized by heating again at 800° C. for one hour in the electric furnace. A calcined powder sample to be used in an animal experiment was thus prepared and sealed in a clean glass ampoule.

The powder sample was subjected to the X-ray diffractiometry to ascertain that the sample was composed of the hydroxyapatite crystalline and no other compound was contained therein, and also subjected to a chemical analysis to find that the molar ratio of Ca to P, namely the ratio of m/n, was 1.67 which was coincident with the theoretical composition of a hydroxyapatite compound represented by $Ca_5(PO_4)_3OH$.

Rabbits each having the weight of about 4 kg were selected as the animals used in the following animal experiment. Under intravenous anaesthesia two holes each having a diameter of about 3 mm were drilld through the femur of each rabbit by a spacing of 15 mm. A paste prepared by adding 10 g of said powder with 8 ml of an isotonic sodium chloride solution was injected into the bone marrow space between the two holes. The rabbits were killed from one week to six months after implantation, and after labelling with tetracycline, the femurs were cut crosswise at the portion intermediate of the two holes. The decalcified and undecalcified specimens were prepared from every killed rabbits, and the histological changes of these specimens were observed.

FIG. 1 is a microphotograph (about 200 magnifications) of a crosswise section of the decalcified specimen showing the portion injected with the paste and taken out of the rabbit after one week from the time of implantation.

As will be apparent from the Figure, particles 1 of the apatite calcium phosphate compound are scattered in the young granulation tissue 3, and the osteoid with attendant osteoblast adhered to the peripheral portions of the particles 1. New cancellous bones 2 are formed at the portions where the particles 1 are relatively closer and these newly formed bones crosslink the particles. No giant cells caused by foreign bodies are observed at all. It should be a distinguishing feature that the newly formed bones contact the peripheries of the particles 1 of the apatite calcium phosphate compound without forming any foreign body membrane. This shows that the compound has a remarkably improved compatibility with the living body and a considerably high osteogenic capacity. In the Figure, reference numeral 7 designates the cortical bone.

After four weeks from the time of implantation, all particles of the apatite calcium phosphate compound are connected with each other through the new bones and form an integral and dense body of cancellous bone.

Figure 2:
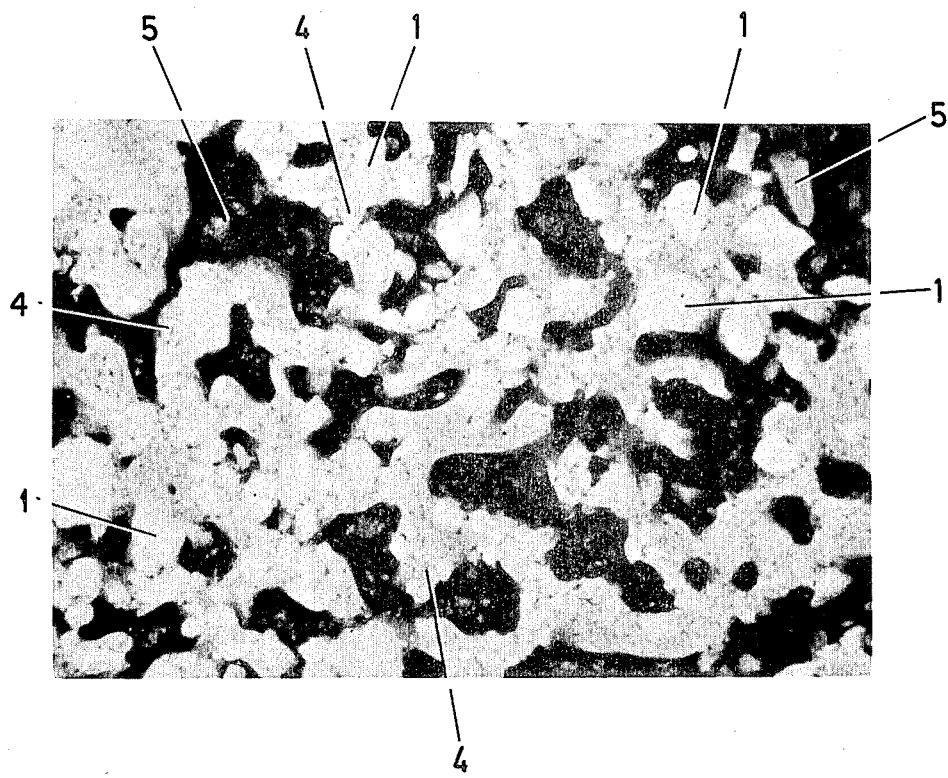
FIG. 2 is a microphotograph similar to FIG. 1, but showing the femur which is taken out of the rabbit killed after the lapse of four weeks from the time of the implantation.

FIG. 2 is a microradiographical photograph (about 200 magnifications) of a crosswise section of the undecalcified specimen showing the portion injected with the paste containing the particles of the apatite calcium phosphate compound and taken out of the rabbit after four weeks from the time of implantation. It is shown that high density particles 1 of the apatite calcium phosphate compound are scatteringly present in a low density new bone beam 4 and that the spacing between the new cancellous bones are filled with the bone-marrow tissue 5. It is also observed that the new bone is formed rapidly without being accompanied with any foreign body reaction and that all of the injected particles 1 are incorporated into the newly formed bone beam 4 and interconnected with each other.

Figure 3:
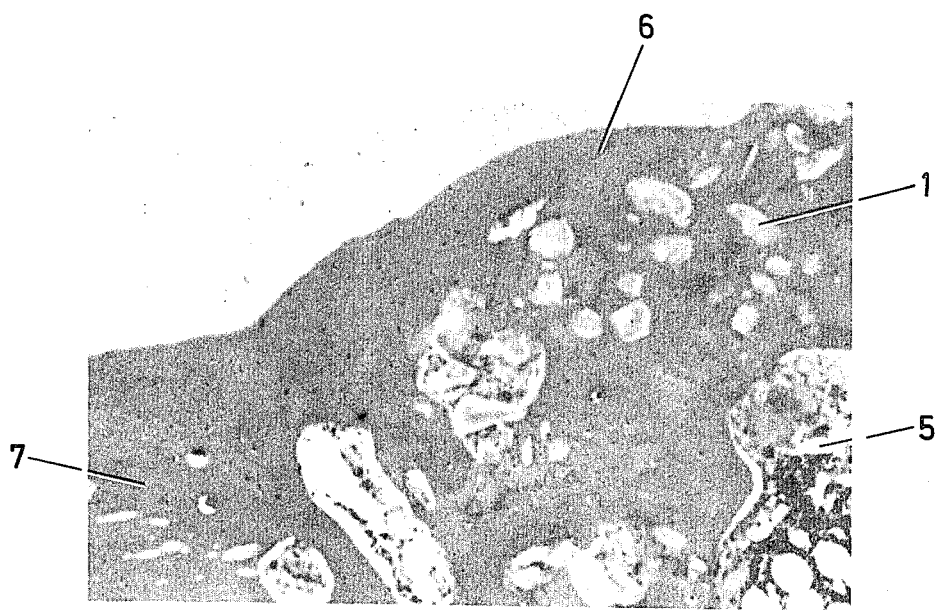
FIG. 3 is a microphotograph similar to FIG. 1, but showing the femur which is taken out of the rabbit killed after the lapse of three months.

FIG. 3 is a microphotograph (about 400 magnifications) of the decalcified specimen showing the drilled portion of the femur of the rabbit taken out of the rabbit after 3 months from the time of implantation. The drilled portion, i.e. the artificially formed defect of bone in the femur (cortical bone) is completely repaired with the new cortical bone 6 and the drilled portion forms an integral body with the surrounding original fumur (cortical bone 7). Although scattering particles 1 are observed at the newly formed bone portion, no foreign body reaction is observed to show excellent compatibility of the filler with the living body. It is also observed that yound bone-marrow tissue 5 is present in the bone-marrow cavity. It is further shown that the bone-marrow tissue at that portion is refreshed and becomes rejuvenated by the injection of the paste of the apatite calcium phosphate compound.

Although bone formation is observed at some portions even after six months after the implantation, the absorption of bone prevails in the bone-marrow cavity and the cancellous bone beams are reduced in number as a whole and become coarser. On the other hand, the new bone formed at the drilled portion is changed to the cortical bone to coalesce with the surrounding original femur. This shows that formation of new bone in the defect and in the bone-marrow cavity does not continued unlimitedly but is adapted for the functional demand of the living body ultimately. In view of this fact, the filler of the invention should be appreciated to be an ideal filler material.

EXAMPLE 5

A calcium phosphate compound synthesized by the wet process was dehydrated and dried to form a cake which was calcined at 1000° C. for 2 hours. The crystal grain size was measured by a scanning electron microscope to find that the average crystal grain size was 0.2 microns, the minimum crystal grain size was 0.1 microns and the maximum crystal grain size was 0.4 microns. This cake was pulverized in a ceramic pot mill to obtain a powder sample which passed a net of 149-micron meshes. The powder sample was subjected to the X-ray diffractiometry to ascertain that the sample was composed of the crystalline hydroxyapatite and no other compound was contained therein, and also subjected to a chemical analysis to find that the molar ratio of Ca/P was 1.63. This powder sample was heated again at 500° C. for 5 hours to be sterilized. A powder sample to be used in an animal experiment was thus prepared and sealed in a clean glass ampoule.

A portion of the cortical bone of the femur of an adult rabbit having the weight of about 4 kg was removed to artifically form a defect of about 2 mm × 5 mm. One part by weight of cancellous bone taken up from the rabbit per se was mixed with one part by weight of the powder of said apatite calcium phosphate compound, and 0.3 part by weight of distilled water was additionally added and kneaded to be plasticized. The plasticized mixture was filled in said defect formed in the bone. The same operations were performed on a group of rabbits which were killed one after another. The portion of the femur containing the defect was cut crosswise to prepare a histological specimen therefrom, and the histological change was observed.

After one week from the operation, appreciable formation of new bones was observed in the neighbourhood of the particles of the apatite calcium phosphate compound, and the particles of the apatite calcium phosphate compound and the autoplastically implanted bone pieces were interconnected with each other by the crosslinking structure of said new bones without any foreign body reaction occurring. After four weeks, considerable development of growth of a new bone beam was observed, and all of the particles of the apatite calcium phosphate compound and the cancellous bone pieces were interconnected by the new bone beams, whereby the portion filled with the filler was made of the cancellous bone tissue in its entirety. After 3 months from the operation, it was observed that said cancellous bone tissue was changed to the cortical bone tissue to coalesce with the surrounding original femur so that the artificially formed defect of bone was completely repaired. This result shows that the shortage in autoplastically taken-up bone may be supplemented with powders of calcium phosphate compound having the apatite crystalline structure to be filled in a defect of bone, whereby the object of therapy can be attained for a shorter period of time according to the present invention.

Comparative Example 1

A high purity alumina powder produced by Iwatani Kagaku K.K. (Trade Name: RA-30, $Al_2O_3=99.9\%$, 100% passing through a net of 149-micron meshes) was used. Following a similar procedure as in the preceding Examples, a paste was prepared from said alumina powder which was injected into the bone-marrow cavity of the femur of a group of rabbits. The progress of new bone formation was investigated.

Figure 4:
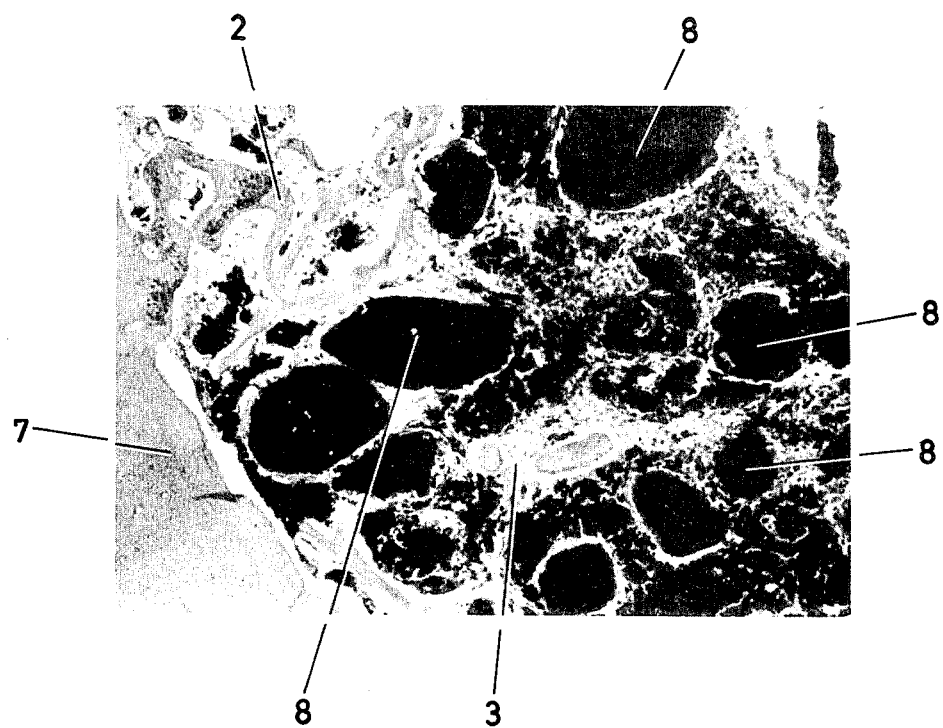
FIG. 4 is a microphotograph similar to FIG. 1, but showing the femur having a hole filled with an alumina powder in place of the filler of the invention and being taken out of the rabbit killed after the lapse of one month.

FIG. 4 is a microphotograph (about 400 magnifications) of a decalcified histological specimen obtained by cutting the femur of a rabbit after one month from the operation. In view of the fact that no appreciable giant cells nor membrane caused by foreign bodies was present in the vicinity of the alumina particles, it is considered that the particles have good compatibility with the living body. Although the alumina particles 1 are scattered in the granulation tissue 3, no new bone is formed in the neighbourhood thereof. Nevertheless a few new cancellous bones 2 which are considered to be formed under the stimulation of the injected paste is observed at the vicnity of the cortical bone 7, it is seen that the alumina particles 8 have no osteogenic capacity (Under a certain stimulation, some new bones are formed in the bone-marrow.)

Comparative Example 2

Figure 5:
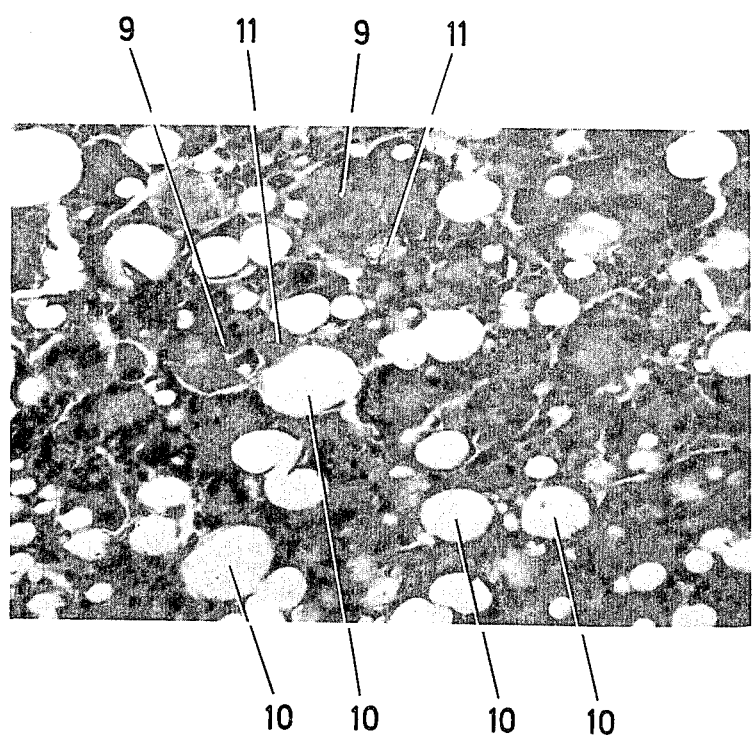
FIG. 5 is a microphotograph similar to FIG. 4, but showing the femur having a hole filled with a commercially available organic bone cement in place of the alumina powder.

A paste was prepared from a commercially available organic bone cement powder (produced by Howmedica Co.; a polymethylmethacrylate resin sold under the Trade Name of "Simplex"). This paste was injected into the bone-marrow of the femur of a rabbit similarly as in the preceding Examples, and the histological change of the injected portion was observed. FIG. 5 shows a microphotograph (about 200 magnifications) of a decalcified histological specimen of the injected portion after one month from the operation.

The bone-marrow of the femur injected with the bone cement paste is filled with giant cells 9 caused by foreign bodies shows the intensive foreign body reaction, and no formation of new bone is observed anywhere. It is also observed that the particles 11 of the Simplex are present scatteringly and fat spots 10 are present here and there.

Although the present invention has been described with reference to the specific examples thereof, it should be understood that various modifications and variations can be easily made by those skilled in the art without departing from the sprit of the invention. Accordingly, the foregoing disclosure should be interpreted as illustrative only and not to be interpreted in a limiting sense. The present invention is limited only by the scope of the following claims.

What is claimed is:

1. A method of treating bones with a filler, wherein defects or hollow portions of bones are filled with fluidized or plasticized powders of a calcium phosphate compound having the apatite crystalline structure of each crystal grain size of from 50 Å to 10 microns and represented by the general formula of $Ca_m(PO_4)_nOH$ ($1.33 \leq m/n \leq 1.95$), and wherein at least a portion of said filler is filled in to reach the bone-marrow cavities of said bones.

2. A method as claimed in claim 1, wherein the crystal grain size ranges from 200 Å to 3 microns.

3. A method as claimed in claim 1, wherein the particle size distribution of said powders of said calcium phosphate compound having the apatite crystalline structure is such that powders each having the particle size of 300 microns or less occupy at least 90% of the total weight.

4. A method as claimed in claim 3, wherein at least 90% by weight of said powders each have the particle size of 150 microns or less.

5. A method as claimed in claim 1, wherein said calcium phosphate compound having the apatite crystalline structure is an artificially synthesized compound prepared by a wet, dry or hydrothermal process.

6. A method as claimed in claim 1, wherein said calcium phosphate compound having the apatite crystalline structure is synthesized by a wet process and calcined at a temperature of from 500° C. to 1100° C.

7. A method as claimed in claim 1, wherein said calcium phosphate compound having the apatite crystalline structure is sintered at a temperature of from 1100° C. to 1350° C.

8. A method as claimed in claim 1, wherein said filler is fluidized or plasticized by the addition of water or an isotonic sodium chloride solution.

9. A method as claimed in claim 1, wherein said filler is granulated.

10. A method as claimed in claim 9, wherein said granulated filler is sintered at a temperature of from 1100° C. to 1350° C. to form a sintered particle having at least 30% pores.

11. A method as claimed in claim 10, wherein at least 50% of said pores have the diameters of at least 100 microns.

12. A method as claimed in claim 9, wherein the granulated filler is sintered and then powders of said calcium phosphate compound having the apatite crystalline structure are added to the granulated filler thus sintered.

13. A method as claimed in claim 12, wherein the content of said granulated and sintered filler is 30% by weight or less.

14. A method as claimed in claim 1, wherein cancellous bone is added to said filler.

15. A method as claimed in claim 14, wherein said cancellous bone is an autoplastic bone.

16. A method as claimed in claim 14, wherein said cancellous bone is introduced from a foreign source and the amount of said added cancellous bone is 50% by weight or less.

* * * * *